US00PP11489P

United States Patent [19]

McGredy

[11] Patent Number: Plant 11,489

[45] Date of Patent: Aug. 22, 2000

[54] GRANDIFLORA ROSE PLANT NAMED 'MACHAHEI'

[75] Inventor: Sam McGredy, Auckland, New Zealand

[73] Assignee: Edmunds' Roses, Wilsonville, Oreg.

[21] Appl. No.: 09/152,708

[22] Filed: Sep. 14, 1998

[51] Int. Cl.[7] ..... A01H 5/00

[52] U.S. Cl. ..... Plt./139

[58] Field of Search ..... Plt./136, 138, 139

[56] References Cited

U.S. PATENT DOCUMENTS

P.P. 5,341 11/1984 Warriner ..... Plt./139

P.P. 6,083 1/1988 Warriner ..... Plt./139

P.P. 6,264 8/1988 Olesen et al. ..... Plt./139

OTHER PUBLICATIONS

UPOV–ROM, 1999/02, Plant Variety Database, GTI Jouve Retrieval Software, citation for 'Machahei'.

*Primary Examiner*—Howard J. Locker

*Attorney, Agent, or Firm*—Christie, Parker & Hale, LLP

[57] ABSTRACT

A new variety of grandiflora rose suitable for garden decoration, having flowers of red coloration.

1 Drawing Sheet

BACKGROUND OF THE INVENTION

This invention relates to a new and distinct variety of Grandiflora Rose. The varietal denomination of the new variety is 'Machahei'. The plant is an upright seedling cultivated for outdoor garden decoration. It has as its seed parent the variety known as 'Maclocker' and as its pollen parent the variety known as 'Macnatdeb'.

SUMMARY OF THE INVENTION

Among the features which distinguish the new variety from other presently available and known commercial rose cultivars are the following combination of characteristics: its red flower color, its strong petal substance that resists weather marking and its deep green foliage. 'Machahei' may be asexually propagated by cuttings, budding, grafting, layering or tissue culture.

Asexual reproduction of the new variety by budding as performed in Kern County, Calif., and Clackamas County, Oreg. shows that the foregoing and other distinguishing characteristics come true to form and are established and transmitted through succeeding propagations.

COMPARISON WITH PARENTS

The new rose may be distinguished from its seed parent, 'Maclocker' by the following combination of characteristics: 'Machahei' is a red grandiflora with large flowers while "Maclocker" is a pink blend floribunda with small flowers. 'Maclocker' is heavily petalled with numerous petalloids hiding the stamens. 'Machahei' has an average number of petals and stamens are visible when the flower is fully open.

The new variety may be distinguished from its pollen parent, 'Macnatdeb' by the following combination of characteristics: 'MacNatdeb' is a very large flowered hybrid tea of 50 or more petals with flower color medium red on the upper side of the petals and straw yellow on the reverse and the new variety has about 30 to 35 petals.

BRIEF DESCRIPTION OF ILLUSTRATION

The accompanying photograph illustrates specimens of flowers of the new variety from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE VARIETY

The following description is of rose plants of the new cultivar grown outdoors in Wilsonville, Oreg. in the month of October. Phenotypic expression may vary with environmental, cultural and climatic conditions, as well as differences in conditions of light and soil.

FLOWER

The new variety bears its flowers sometimes singly, usually in clusters of three to five or more per stem. Flowers are borne in regular flat to rounded clusters on strong medium to long stems (about 30 to about 50 cms.) for the class. Outdoors, the plant blooms very freely and abundantly and nearly continuously during the growing seasons. The flowers have a slight to moderate spicy fragrance.

BUD

The peduncle is of average length for the class (about 7 to about 10 cms.), and usually stiff. It is almost entirely smooth, with very few stipitate glands, and very few prickles. Peduncle color is between 182A and 183D.

Before the calyx breaks, the bud is small to medium size for the class (about 1.25 to about 1.33 cms. in diameter at the widest point), medium in length (about 3 to about 4 cms.), and ovoid in shape with a conspicuous neck. The surface of the bud bears few foliaceous appendages and stipitate glands, usually with slender foliaceous parts extending beyond the tip of the bud equal to ½ or more of its length. Bud color is between 135C and 138D suffused with near 183A giving an overall appearance of brownish red.

The inner surface of the sepals is covered with fine wooly tomentum; sepal margins are lined with a few stipitate glands and hairs.

As the petals open, the bud is medium to large for the class (about 2.5 to about 3 cms. in diameter at the widest point), medium length (about 3 to about 4 cms.), and pointed to ovoid in form. The color of the under surfaces of the newly opened petals is between 45A and 46A. The color of the upper surfaces of the newly opened petals is between 45B and 46B. The bud opens up well and is generally not prevented from opening by wet, cold, hot or dry weather.

BLOOM

When fully open, the bloom is medium to large for the class, ranging from about 8 to about 10 cms. in diameter. Petalage is double with about 30 to 35 petals and none or a few petaloids arranged regularly. When partially open, the bloom form is somewhat cupped to high centered, and the petals are somewhat spiraled to cupped with petal edges somewhat rolled outward. When fully open, the bloom form is moderately flat to cupped, and the petals are more or less loosely cupped with petal edges rolled outward.

PETALS

The substance of the petals is crisp and petals are of medium thickness. Upper surfaces are very shiny to velvety and under surfaces area moderately velvety. The outer petals are moderately ovate to obovate in shape with apices somewhat rounded and sometimes notched with one notch. The inner petals are narrowly round to deltoid in shape with apices moderately rounded.

NEWLY OPENED FLOWER

The under surface of the outer petals is between 46C and 47B. The upper surface of the outer petals is between 44B and 45B.

The under surface of the intermediate petals is between 46D and 47C. The upper surface of the intermediate petals is between 43B and 43C.

The under surface of the inner petals is between 45 D and 46C. The upper surface of the inner petals is between 43A and 44A.

The general tonality of the newly opened flower is between 43D and 44B.

THREE DAY OLD FLOWER

The under surface of the outer petals is between 47A and 46D. The upper surface of the outer petals is between 44B and 45B.

The under surface of the inner petals is between 47B and 47D. The upper surface of the inner petals is between 44B and 45C. Petal color at point of attachment is near 15C.

The general tonality of the three-day-old flower is between 44A and 44C. Stamens are evident when bloom is fully open.

The petals usually drop off cleanly on the spent bloom fading to 48B only in wet weather on exposed petal edges.

In September, blooms on the bush growing outdoors generally last from three to five or more days. Cut roses grown outdoors and kept at normal indoor living temperatures generally last from three to five days.

MALE REPRODUCTIVE ORGANS

Stamens are average to many in number and are arranged regularly about the pistil and are shorter than the pistil. The filaments, (44C) are short in length, most with anthers. The anthers are moderately small for the class and all open approximately at the same time. Anther color is near to 11B when immature and near to 11A at maturity. Pollen is near to 20A in color.

FEMALE REPRODUCTIVE ORGANS

Pistils vary in number (approximately 40–50). The styles are moderately even, average to long in length, average to heavy in caliper, and loosely separated. Stigma color is near to 11C. Style color is near 47C. Ovaries are ususally few, (8–12) all enclosed in the calyx.

No hips are observed on this variety when grown in Wilsonville, Oreg. Peduncles become brown and necrotic following petal fall.

FOLIAGE

The compound leaves are usually comprised of three to seven leaflets and are borne abundantly. The leaves are medium for the class, (about 16 to about 20 cms. in length and about 11 to about 14 cms. in width at the widest point), leathery in texture, and glossy in finish. The leaflets are medium for the class (about 5 to about 7 cms. in length and about 3.5 to about 5 cms. in width at the widest point), shaped oblong with moderately acute apices and round bases. Their margins are simply serrate.

The upper surface of the mature leaf is between 136A and 139A. The under surface of the mature leaf is between 138A and 138B. The upper surface of the young leaf is near to 187A. The under surface of the young leaf is near to 183A.

The rachis upper side is smooth and shallowly grooved with some stipitate glands on the edges of the grooves. The under side of the rachis is somewhat smooth with few small prickles.

The stipules are medium to long in length with medium width and medium straight points that usually turn out at an angle of more than 45 degrees.

The plant displays above average degree of resistance to powdery mildew and blackspot and rust as compared to other commercial varieties grown under comparable conditions in Wilsonville, Oreg.

GROWTH

The plant has an upright low to medium height habit (to about 110 cms. in height and about 50 to about 60 cms. spread at the widest point), with very full branching. It displays vigorous growth.

The color of the major stems is between 138A and 139B. They bear many large prickles which are medium length to long for the class (about 0.75 to about 2.25 cms). The large prickles are hooked slightly downward with a long narrow rounded base; prickle color is between 152B and 152C. The major stems bear many small prickles of similar shape and coloration and which are between 152B and 52C in color. There are no hairs.

The color of the branches is between 138A and 139B. They bear many large prickles, which are of similar size and shape to the large prickles on the major stems; prickle color is between 152B and 152C. The branches bear many small prickles of similar shape and coloration and which are between 152B and 152C in color. There are no hairs.

The color of the new shoots is between 141D and 143C sometimes lightly suffused with near to 183A. They bear many large prickles, which are of similar size and shape to the large prickles on the major stems; prickle color is between 183A and 185A. The shoots bear many small prickles of similar shape and coloration and which are between 183A and 185A in color. There are no hairs.

I claim:

1. A new and distinct rose plant of the variety substantially as shown and described.

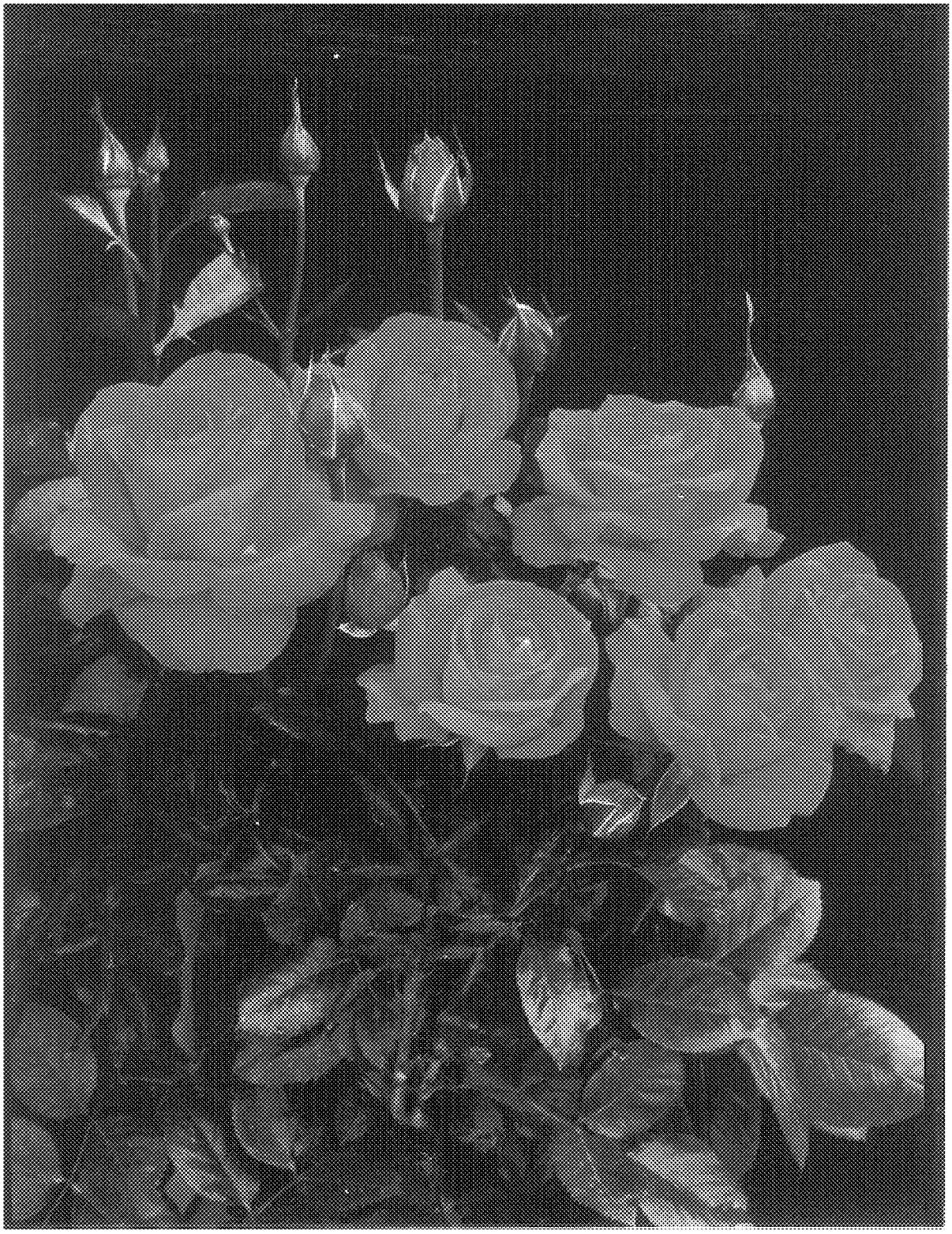

* * * * *